United States Patent [19]

Arora

[11] Patent Number: 5,344,924
[45] Date of Patent: Sep. 6, 1994

[54] SOLVENT-FREE SYNTHESIS OF ETHEREALLY SUBSTITUTED BLOCKED MONOSACCHARIDES AND THE SELECTIVE HYDROLYSIS THEREOF

[75] Inventor: Sudershan K. Arora, Lansdale, Pa.

[73] Assignee: Greenwich Pharmaceuticals, Incorporated, Ft. Washington, Pa.

[21] Appl. No.: 44,085

[22] Filed: Apr. 6, 1993

Related U.S. Application Data

[63] Continuation of Ser. No. 658,311, Feb. 20, 1991, abandoned.

[51] Int. Cl.$^5$ ............................................. C07H 1/00
[52] U.S. Cl. ................................. 536/124; 536/18.5; 536/120
[58] Field of Search ..................... 536/124, 18.5, 120

[56] References Cited

U.S. PATENT DOCUMENTS

| | | | |
|---|---|---|---|
| Re. 30,354 | 7/1980 | Gordon | 536/17.9 |
| Re. 30,379 | 8/1980 | Gordon | 536/17.9 |
| Re. 32,268 | 10/1986 | Gordon | 514/25 |
| 1,488,355 | 3/1924 | Lilienfeld | 536/120 |
| 2,715,121 | 8/1955 | Glen et al. | 536/120 |
| 3,939,145 | 2/1976 | Gordon | 536/17.9 |
| 3,939,146 | 2/1976 | Gordon | 536/17.9 |
| 3,965,262 | 6/1976 | Gordon | 514/25 |
| 4,016,261 | 4/1977 | Gordon | 536/120 |
| 4,017,608 | 4/1977 | Gordon | 536/120 |
| 4,056,322 | 11/1977 | Gordon et al. | 536/120 |
| 4,251,520 | 2/1988 | Bruzzese et al. | 514/25 |
| 4,735,934 | 4/1988 | Gordon | 514/25 |
| 4,738,953 | 4/1988 | Gordon | 514/25 |
| 4,996,195 | 2/1991 | Ronsen et al. | 514/23 |
| 5,010,058 | 4/1991 | Ronsen et al. | 514/25 |

OTHER PUBLICATIONS

Wayne G. Riskin, et al., "Amiprilose Hydrochloride for Rheumatoid Arthritis", Annals of Internal Medicine, vol. 111, No. 6, Sep. 15, 1989, pp. 455–465.

*Primary Examiner*—Johnnie R. Brown
*Assistant Examiner*—Everett White
*Attorney, Agent, or Firm*—Finnegan, Henderson, Farabow, Garrett & Dunner

[57] ABSTRACT

A solvent-free method for synthesizing an ethereally-substituted, blocked monosaccharide comprising the steps of:

1) mixing, in the absence of solvent, a partially blocked monosaccharide unblocked at one position, an alkyl halide or a substituted alkyl halide, and an anhydrous alkali base;
2) heating the mixture to a temperature sufficient to allow the mixture to react;
3) maintaining the mixture at a suitable temperature for a time sufficient to form an ethereally-substituted blocked monosaccharide and drive off any water produced;
4) removing any unreacted alkyl halide or substituted alkyl halide from the mixture;
5) recovering the ethereally-substituted blocked monosaccharide product from the mixture; and, optionally,
6) selectively hydrolyzing the ethereally-substituted blocked monosaccharide product to remove one or more of the acetal blocking groups.

18 Claims, No Drawings

SOLVENT-FREE SYNTHESIS OF ETHEREALLY SUBSTITUTED BLOCKED MONOSACCHARIDES AND THE SELECTIVE HYDROLYSIS THEREOF

This application is a continuation of application Ser. No. 07/658,311, filed Feb. 20, 1991, now abandoned.

FIELD OF THE INVENTION

This invention relates to the solvent-free synthesis of ethereally-substituted monosaccharides and to derivatives thereof formed by selective hydrolysis.

BACKGROUND OF THE INVENTION

The process of this invention allows the economical solventfree synthesis of ethereally-substituted monosaccharides such as amiprilose, 1,2-O-isopropylidene-3-O-3'-(N',N'-dimethylamino-n-propyl)-α,D-glucofuranose and its' hydrochloric acid salt (amiprilose HCl).

Monosaccharides have been previously reported to have immunomodulatory activity, especially in infectious disease models. See Muchmore A. V., et al., *Immunobiology* 1981; 158:191–206; Rasanen L., Cell Immunol 1981; 58:19–28; Brunda M. J., et al., *Int J Cancer* 1983; 31:373–9; and Nencioni L., et al., *Infect Immun* 1985; 47:534–9. Several other glucofuranosides have been described as having potent anti-inflammatory properties and low toxicity. See Tannenbaum J., et al., *Prostaglandins* 1979; 17:337–50; Goi A., et al., *Arzneimittelforschung* 1979; 29:986–90; Jaques R., *Pharmacology* 1977; 15:445–60; Riesterer L., et al., *Pharmacology* 1970; 3:243–51; Jaques R., *Pharmacology* 1970; 4:193–202; Kuzuna S. et al., *Yakuri to Chiryo* August 1974; 2:997–1010; Bianchi C., Agents Actions 1981; 11:750–61; and Di Rosa M., *Arch Int Pharmacodyn Ther* 1968; 173:162–72. Ethereally-substituted monosaccharides and the therapeutic activity thereof are described in U.S. Pat. Nos. Re. 30,354 and Re 30,379; the disclosure of which are incorporated herein by reference.

The ethereally-substituted monosaccharide amiprilose has been reported to have anti-inflammatory properties in animal models predictive for anti-rheumatic effects in humans, including adjuvant arthritis, experimental monoarticular arthritis, and carageenan footpad edema See Gordon P., *Inflammation, Mechanisms and Treatment*, Willoughby D. A, Giroud J. P, eds., Baltimore: University Park Press; 1980:169–80. Other preliminary studies have suggested that amiprilose has anti-rheumatic effects in a type II collagen arthritis model and antiproliferative properties in cultured synoviocytes See Kieval R. I., et al., *Arthritis Rheum* 1988; 31:71N. The drug has also been reported to exhibit immunomodulatory properties, including macrophase stimulating effects. Morrison C. J., et al., *Antimicrob Agents Chemmother* 1984; 26:74–7; Hadden J. W., Cancer Treat Rep 1978; 62:1981–5; and Hadden J. W., et al., *Int J Immunopharmacol* 1979; 1:17–27. Amiprilose has also shown effects on circulating T8 lumphocytes in rheumatoid arthritic patients Weinblatt M. E, et al., *J Rheumatol* 1987; 14:859–60. Recently, patients treated with amiprilose have shown sequential decreases in serum interleukin-2 receptor levels that correlated with improvement in clinical measures of disease activity suggesting the possibility that amiprilose may diminish T-cell activation in patients responsive to the drug. Campen (D. H., et al., *Arthritis Rheum.* 1983; 31:1358–64. Most recently, Amiprilose HCl has been shown to be effective in the treatment of rheumatoid arthritis. Riskin W. G., et al. *Ann. Int. Med.* 1989; 111:455–465.

According to the method of U.S. Pat. No. 2,715,121, the synthesis of ethereally-substituted monosaccharides involves the reaction of a monosaccharide derivative which is blocked with one or more organo groups in the hydroxyl group positions adjacent to the desired position to be substituted. The blocked monosaccharide can be dissolved in an organic solvent such as dioxane, tetrahydrofuran or benzene and is reacted with a halogenated organo amino compound having the desired carbon chain length and configuration in the presence of a base such as sodium hydroxide. After the reaction is complete, selective removal of one or more blocking groups may be accomplished by hydrolysis under specific conditions.

With the above method, amiprilose HCl is prepared by first reacting a mixture of a 1,2:5,6-di-O-isopropylidene-α,D-glucofuranose (DAG), a hydrochloric acid salt of chloro-dimethyl aminopropane, and sodium hydroxide in dioxane at reflux for at least 9 to 11 hours to yield 1,2:5,6-Di-O-isopropylidine-3-O-3-(N'N'-dimethylamino-n-propyl)-α,D-glucofuranose. The total time taken to produce one batch of the diacetal blocked hexose ether in this first step from initial preparation of the reaction through isolation of the final product is about 50 hours. If the product is then hydrolyzed in aqueous environment to yield the desired amiprilose HCl, an additional 70 hours is required. Thus, the total time required for the overall synthesis is approximately 120 hours.

The process of U.S. Pat. No. 2,715,121 suffers from numerous disadvantages. First, a significant amount of time is required to synthesize and workup any desired product. Second, the process uses dioxane as a solvent which is toxic in nature and requires a special permit to use it in chemical plants. Third, hydrochloric acid salts of amino substituted alkylhalides, such as chloro-dimethylaminopropane hydrochloride (DMCP HCl), used in the synthesis of amiprilose, are significantly more expensive than the corresponding free base. Finally, the prior art process requires the disposal of expensive dioxane-containing waste which costs about $1.50 to $3.50 per liter.

The selective hydrolysis step also adds a significantly amount of time to the prior art process. The hydrolysis is generally carried out in refluxing solvent for approximately 2–4 hours. The aqueous hydrolysis medium requires pH adjustment which results in the production of mineral salts such as NaCl which precipitate out along with the amiprilose HCl and contaminate the product. The process often requires a series of steps where the mother liquor is concentrated and the precipitated product collected in order to obtain a satisfactory yield. Additionally, the product often requires a milling step to form a powder prior to pharmaceutical use.

Copending U.S. patent application Ser. No. 07/433,460, filed Oct. 1, 1990, now abandoned and commonly assigned to Greenwich Pharmaceuticals, Inc., discloses a solid phase Williamson's synthesis of diacetal blocked cyclic hexose ethers. The method comprises the steps of blending together, in the solid phase, a partially blocked acetal of a hexose sugar which is unblocked at one hydroxyl position of the hexose and an excess of anhydrous sodium hydroxide. The blended materials are reacted at a temperature and for a time sufficient to form water and a hexose sodium salt at the unblocked sugar position. Substantially all the water formed by the reaction is removed. The remaining blend of the hexose sodium salt product and unreacted, excess sodium hydroxide is mixed with an alkyl halide or substituted alkyl halide such that the hexose sodium salt condenses with the alkyl halide or substituted alkyl halide. The condensation reaction is conducted at a temperature sufficient to produce the ethereally-substituted hexose monosaccharide and a sodium halide. Finally, the sodium halide is removed to yield a purified ethereally-substituted hexose monosaccharide. The product may then undergo selective hydrolysis to remove the blocking groups.

SUMMARY OF THE INVENTION

An object of this invention is to provide an economical process for the synthesis of ethereally-substituted monosaccharides and particularly diacetal blocked cyclic hexose ethers. This economic process eliminates the use of organic solvents, reduces reaction time, eliminates the tedious and lengthy work-up procedure and also eliminates completely the expensive organic solvent waste which is generated in the prior art process.

A second object of the present invention is a process which produces ethereally-substituted monosaccharides in good yield and high purity.

A third object of the invention is a process which allows for the synthesis and selective hydrolysis of ethereally-substituted acetal blocked monosaccharides to other useful therapeutic agents.

The first two objects and other advantages of the invention are accomplished by a solvent-free method for synthesizing an ethereally-substituted acetal blocked monosaccharide comprising the steps of:
1) mixing together, in the absence of solvent, a partially blocked acetal of a monosaccharide unblocked at one position, an alkyl halide and an anhydrous alkali base;
2) heating the mixture to a temperature sufficient to cause the mixture to react;
3) maintaining the mixture at a suitable temperature for a time sufficient to form an ethereally-substituted acetal blocked monosaccharide and to drive off any water produced;
4) removing any unreacted alkyl halide from the mixture; and
5) recovering the ethereally-substituted acetal blocked monosaccharide product from the mixture.

The third object of the invention is accomplished by employing the above solvent-free synthesis and then selectively hydrolyzing the ethereally-substituted acetal blocked monosaccharide product to remove one or more of the acetal blocking groups.

DETAILED DESCRIPTION

The process for the synthesis of ethereally-substituted monosaccharides, and particularly of acetal blocked cyclic hexose ethers, according to the present invention is a solvent-free synthesis. No solvent is employed as a reaction medium. A liquid is only present in the initial unheated reaction mixture if one of the reactants is a liquid at room temperature.

The reactants are mixed together, heated to temperature sufficient to cause the reaction to go forward and then reacted at a second temperature reached due to the exothermic character of the reaction. The reaction is maintained at this second reaction temperature for a time sufficient to form the desired ethereally-substituted acetal blocked monosaccharide. The starting materials for the process are a partially blocked acetal of a monosaccharide unblocked at least at one position, an alkyl halide and an anhydrous alkali base.

The monosaccharide used in the present invention can be derived from any known aldose or ketose. The method of this invention can be used with any monosaccharide having one or more free hydroxyl group. Thus, for example, any pentose, hexose or heptose having one or more free hydroxyl groups will undergo ethereal substitution at each hydroxyl group according to the method disclosed here. One of ordinary skill would understand how to adjust the reaction stoichiometry in order to achieve the desired amount of ethereal substitution at the free hydroxyl groups.

It is preferred to employ in the present method a partially blocked acetal hexose monosaccharide unblocked at only one position, that is having only one free hydroxyl group. While the method of this application is entirely general and is not limited to such a hexose, the method will be described in greater detail in reference to this preferred starting material.

The configurations of the various hexoses are well known to those skilled in this art and numerous reference books are available on the subject. For example, see Textbook of Biochemistry, 4th Edition, by West et al. (1966) and the Monosaccharides by Stanek, Cerny, Kocourek and Pacak (1963). The prior art discloses, for example, a total of eight open chain isomers for the reducing hexoses. A hexose monosaccharide may also adopt a five-membered furanose hemiacetal ring structure or a six-membered pyranose hemiacetal ring structure. A furanose ring structure is generally preferred in the method of the present invention. Any of the D-series or the L-series hexoses may be used in practicing the invention, but it is usually preferred to use the D-series.

According to a preferred embodiment of the present invention, the hexoses may be ethereally monosubstituted at any available hydroxyl group and derivatized at one or more of the remaining hydroxyl groups. Substitution at certain positions of specific monosaccharide derivatives result in therapeutically active and useful compounds. For instance, substitution of the 3-O-position of 1,2-O-isopropylidene-D-glucofuranose and the 6-O-position of 1,2-O-isopropylidene-D-glactopyranose or 1,2:3,4-di-O-isopropylidene-D-galactopyranose results in especially valuable compounds.

Diacetal blocked hexoses generally exist as solids at room temperature. Various blocking methods are described in U.S. Pat. Nos. 2,715,121 and 4,056,322, the disclosures of which are incorporated by reference herein. In instances where an aldehyde or ketone is reacted with the hydroxyl groups on adjacent or neighboring monosaccharide carbon atoms, the hexose may be blocked in a plurality of positions, such as, e.g., the 1,2- and/or 5,6-positions. In 1,2:5,6-blocked hexoses, the ring forms between carbons 1 and 4, leaving carbon 3 free to etherize; in the 1,2:3,5-blocked hexoses, the ring forms between carbons 1 and 4, leaving carbon 6 free to etherize; and in 1,2:4,5-blocked hexoses, the ring forms between carbons 2 and 6, again leaving carbon 3 free to etherize. Thus, 1,2:5,6-blocked hexoses may form 3-O ethers, 1,2:3,5-blocked hexoses may form 6-O ethers, and 1,2:4,5-blocked hexoses may also form 3-O ethers. Although acetone is preferred for convenience, the particular blocking compounds or derivatization methods selected are not important so long as it does not interfere with the synthesis method of the present invention, as can be routinely determined by one of ordinary skill in this art by following the disclosure herein.

The most preferred acetal blocked hexose monosaccharide starting material is 1,2:5,6-di-O-isopropylidene-α,D-glucofuranose (DAG). DAG is unblocked at the hydroxyl group of carbon three.

The alkyl halide starting material can be a substituted or unsubstituted alkyl halide having 1-12 carbon atoms and may be in the form of a straight or branched chain, a cyclic group or an aromatic group. Preferred alkyl groups include n-propyl, heptyl, benzyl and phenylpropyl. The halide starting materials are generally liquid at ambient temperature. Any alkyl halide having a good halide leaving group may be used in the present invention; preferably chloride or bromide.

The substituted alkyl halide starting material is preferably an amino-substituted alkyl halide. The amino substituent is selected from the group of a secondary amine, tertiary amine and a cyclic amine. The preferred amino-substituted alkyl halides are used as free bases which provides a significant cost savings over the prior art process which employs acid salts of the aminosubstituted alkyl halides. A particularly preferred substituted alkyl halide is chlorodimethylaminopropane (DMCP).

Other preferred substituted alkyl halides are those having hydroxyl groups or cyano groups. Particularly preferred compounds of these classes are chloropropanol and chloropropanenitrile.

The anhydrous alkali base can be any alkaline or alkaline earth base. The preferred base is sodium hydroxide. The base is preferably used in the form of dry flakes.

In the practice of the present invention, a blocked acetal of a monosaccharide is preferably mixed with an excess over the stoichiometric amount of alkyl halide and an excess over the stoichiometric amount of dry base. More preferably, about a 0.1-0.2 molar excess of alkyl halide and about a 2 molar excess of base is used. The excess alkyl halide insures complete reaction while the excess base increases the speed of the reaction. The solvent-free synthesis proceeds, for example, according to the following reactions:

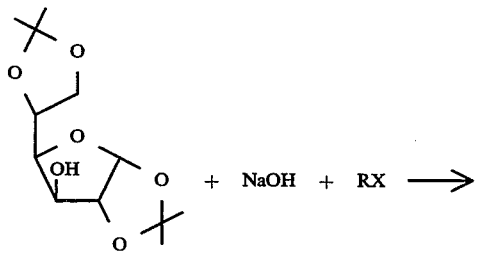

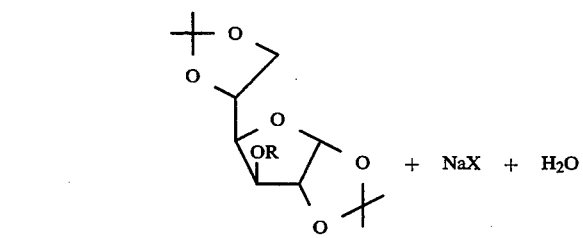

where
R=alkyl substituted alkyl, aminoalkyl, benzyl, or phenylpropyl;
X=Cl or Br

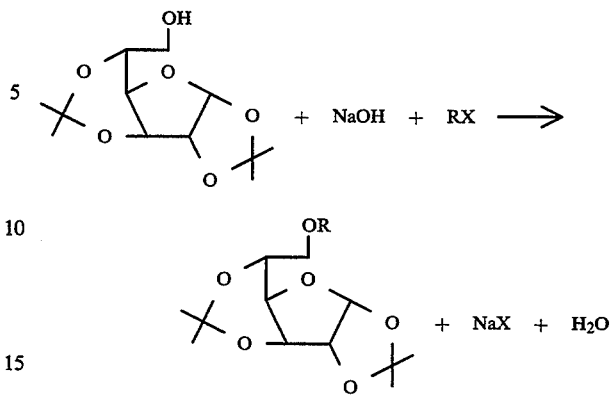

where
R=alkyl substituted alkyl aminoalkyl, benzyl, or phenylpropyl;
X=Cl or Br

The mixture of these reactants is heated to a first temperature where the reaction is initiated Since the reaction is exothermic, once the reaction is initiated the temperature will increase to a level at which the reaction proceeds to completion. For example, when the monosaccharide is DAG and the alkyl halide is DMCP, the reaction generally is initiated at about 80° C. and then increases in temperature and proceeds to completion at about 110° C.-120° C. When DAG is reacted with heptyl bromide the initiation temperature is about 110° C. and the reaction temperature reached as a result of the reaction's exothermic character is about 135° C. The exact initial temperature utilized is not critical and will depend upon the particular reactants, but must be sufficient to initiate the reaction so that the second reaction temperature is reached and the reaction can proceed to completion at which point substantially all of the monosaccharide has been reacted.

Due to the exothermic character of the reaction, it is only necessary to heat the reaction to an initial temperature where the reaction will be initiated. The reaction temperature will then naturally increase to a second temperature suitable to allow the reaction to go to completion. Other means and methods, of heating the reactants to accomplish the desired reaction will be apparent to those of ordinary skill in the art.

In general, a reaction time of only about 30 to about 120 minutes is required for complete conversion. The reaction time generally depends on the batch size but levels off somewhat when using larger scales. For example, mixture of 30 g of DAG, 13.2 g sodium hydroxide (flakes), and 14.8 g DMCP free base heated first to about 80° C. then increasing to about 120° C. required a reaction time of about 30 minutes. When the batch size is increased from 30 g to 260 g of DG, the reaction time increased to about 2 hours. Under the same conditions, when 1 kg of DAG is used the reaction time is also found to be 2 hours for complete conversion. Even when 4kg of DAG is used, the reaction time is still 2 hours. Thus, the present process represents a significant time savings over the process of the prior art which requires heating the reactants reflux in dioxane for at least 9-11 hours.

As Equations (I) and (II) illustrate, water is also a product of the solvent-free reaction. An advantage of the present invention is that the water formed is essentially eliminated from the desired product by maintaining the reaction products at the reaction temperature for a sufficient time to complete the reaction and to drive off the water. The water may be removed by simple evaporation. Preferably, the reaction may be conducted under reduced pressure which facilitates removal of the water vapor. Removal of the water produced is important in the isolation and further reaction of the ethereally-substituted product.

Any excess alkyl halide is also removed from the reaction mixture after the reaction is complete. The alkyl halide is preferentially removed under reduced pressure. Heating may or may not be applied if required to effectively remove the excess alkyl halide. Such experimental determinations are within the level of ordinary skill in the art.

The final ethereally-substituted diacetal blocked product is preferably recovered from the reaction mixture by dissolving the product in an organic solvent which is immiscible with water. A preferred solvent is hexane. Other suitable solvents are ether, dichloromethane, dichloroethane, chloroform, etc. The amount of solvent employed is that which is sufficient to dissolve all of the ethereally-substituted product leaving behind as solid precipitate any unreacted base and unwanted salt products. The solution may then be filtered and water added to the filtrate to yield a solution containing a separate aqueous phase and a separate organic phase. Any extraneous excess base or salts are thus removed into the aqueous phase. The phases are then separated, the aqueous phase descended and the organic phase is dried over a drying agent. Standard drying agents such as are known in organic synthesis may be used. Anhydrous $MgSO_4$ or $Na_2SO_4$ are preferred drying agents.

The resulting organic phase solution is again filtered to remove the drying agent and the organic solvent is removed by conventional techniques preferably under reduced pressure with or without heating, to yield the desired product as a viscous liquid.

The progress of the solvent-free synthesis can be effectively monitored by gas chromatography and/or thin layer chromatography. Either the disappearance of starting material or amount of product produced may be monitored.

The solvent-free synthesis of this invention is useful in but not limited to, for the preparation of.

1,2:5,6-Di-O-isopropylidene-3-O-3'-(N'N'-dimethylamino-n-propyl)-α,D-glucofuranose;
1,2:5,6-Di-O-isopropylidene-3-O-heptyl-α,D-glucofuranose;
1,2:5,6-Di-O-isopropylidene-3-O-benzyl-α,D-glucofuranose;
1,2:5,6-Di-O-isopropylidene-3-O-(n-butyl)-α,D-glucofuranose;
1,2:5,6-Di-O-isopropylidene-3-O-1'-(3'-phenyl-n-propyl)-α,D-glucofuranose;
1,2:5,6-Di-O-isopropylidene-3-O-3'-(N',N'-dimethylaminoisobutyl)-α,D-glucofuranose;
1,2:3,5-Di-O-isopropylidene-6-O-(n-heptyl)-α,D-glucofuranose;
1,2:3,5-Di-O-isopropylidene-6-O-benzyl-α,D-glucofuranose;
1,2:5,6-Di-O-isopropylidene-3-O-benzyl-α,D-glucofuranose;
1,2:4,5-Di-O-isopropylidene-3-O-3'-(N',N'-dimethylamino-N-propyl)-D-fructopryanose The present invention also involves the selective hydrolysis to remove one or more blocking group from a partially blocked ethereally-substituted hexose monosaccharide using about 1 equivalent of $H_2O$ and an acidified-alcohol environment. Any alcohol such as methanol, ethanol or propanol, etc. may be used. Ethanol is preferred. Any strong acid may be used such as perchloric acid, $HClO_4$ or hydrochloric acid HCl. HCl is preferred. The amount of acid employed should be 10–50% per volume of alcohol, preferably 20% HCl in ethanol for the synthesis of amiprilose HCl. Use of another acid should result in the same $H^+$ concentration. The preferred acidified alcohol is ethanolic HCl.

The selective hydrolysis of an ethereally-substituted, acetal blocked monosaccharide where the ether substituent is a substituent which does not contain an amino group may be carried. out according to generally known procedures. The isolated product from the solvent-free synthesis is first dissolved in the alcoholic solvent, preferably ethanol, and cooled to about 0°–10° C. The acidified-alcohol, preferably 30% HCl in ethanol or 30% $HClO_4$ in ethanol, is then added to the solution. After the hydrolysis is complete, the reaction is neutralized, preferably with an aqueous solution of potassium carbonate, and the solvent stripped off to leave a solid or an oil. A suitable solvent for the product, such as ethylacetate or ether, is then added in an amount sufficient to dissolve all of the hydrolyzed product and leaving any unwanted salts behind as solids. This solution is then filtered and the solvent removed to yield the desired selectively hydrolyzed product generally in the form of a viscous liquid.

When the selective hydrolysis involves an amino-containing ethereally substituted, acetal blocked monosaccharide, the amino group is first neutralized, then additional acid is added to accomplish the hydrolysis. The hydrolysis yields the desired product in the form of an acid salt which then precipitates out of solution as a crystalline solid. It is advantageous therefore to use about 2 moles of $H_2O$ per mole of blocking group to be removed. When excess water is present the selectively hydrolyzed product becomes increasingly soluble in the acidified-alcohol medium and is not easily recovered. Thus, the overall yield may be reduced.

There are numerous advantages to the hydrolysis aspect of this invention particularly in regard to the amino-containing compounds. Under the prior art method, the reaction takes place in refluxing solvent and the reaction medium requires pH adjustment. Such pH adjustments result in the production of mineral salts, such as sodium chloride. These salts crystallize out along with the selectively hydrolyzed product and thus contaminate the product. In contrast, the present hydrolysis can be easily carried out at low temperatures such as obtained with an ice bath or even at room temperature. The rate of conversion is fast compared with prior art and affords the desired product directly without additional workup. With the present method, the selectively hydrolyzed product, such as amiprilose HCl, crystallizes out of solution during hydrolysis and can be readily collected by filtration. Washing the crystalline product with alcohol and vacuum drying is all that is required to finish the product. With the process of this invention, the purity of the product is generally greater than 99.4% and the yield is comparable or better than other known preparations.

One of the surprising outcomes of this new hydrolysis procedure is the fineness of the crystalline amiprilose HCl. Current manufacturers require a milling step to powder the product prior to pharmaceutical use. The need for milling is avoided by the present process. Also, in the existing prior art process multiple crops of amiprilose HCl are required to obtain 90% yields. Whereas in the present process a 96% yield of pure amiprilose HCl is obtained in the first crop.

The present invention is not limited to removal of only a single blocking group. One or more of the remaining blocking groups can also be removed by further hydrolysis if desired.

Using this entire process of the present invention, the time for the synthesis of the ethereally-substituted monosaccharide amiprilose HCl starting from DAG (which includes the solvent-free synthesis and subsequent hydrolysis) is reduced from approximately 120 hours as in the prior art to 48 hours. This time, which also includes 12 hours for drying the final product, constitutes therefore a net saving of 72 hours per batch. The complete synthesis of amiprilose HCl according to the present invention is shown by the following reaction scheme:

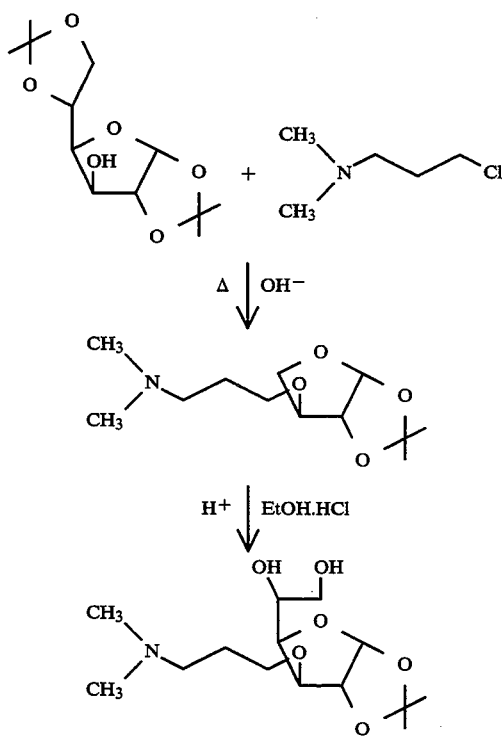

The following examples are provided to illustrate, not limit, the present invention.

EXAMPLE 1

Solvent-free synthesis of 1,2:5,6-di-O-isopropylidene-3-O-3'-(N',N'-dimethylamino-n-propyl)-α,D-glucofuranose.

The reactants, 30 g of 1,2:5,6-di-O-isopropylidene-α-D-glucofuranose (DAG), 13.2 g of anhydrous NaOH flakes and 14.8 g of free base chloro-dimethylaminopropane (DMCP) are mixed together in a flask and heated initially to 80° C. The reaction temperature then increases to 120° C. and remains at that temperature for about 2 hours. The progress of the reaction is followed by GC and TLC. After the reaction is complete, the excess DMCP is removed under reduced pressure. The product residue is dissolved in 100 ml hexane, and filtered. Water is then added (as two 25 ml washings) to the filtrate, the phases are separated and the organic phase dried over anhydrous MgSO₄. The solvent is then removed to give a viscous liquid. The yield of 1,2:5,6-di-O-isopropylidene-3-O-3'-(N',N'-dimethylamino-n-propyl)-α,D-glucofuranose is 85–98% and is more than 97% pure. This product may then be used directly in the selective hydrolysis reaction of Example 2.

EXAMPLE 2

Synthesis of Amiprilose HCl, 1,2-O-isopropylidene-3-O-3'-(N',N'-deimethylamino-n-propyl)-α,D-glucofuranose hydrochloride, by selective hydrolysis using ethanolic-HCl.

To a flask containing 2.5 kg of 1,2:5,6-di-O-isopropylidene-3-O-3'-(N',N'-dimethylamino-n-propyl)-α,D-glucofuranose (as obtained in Example 1) and 5 L of absolute ethanol is added 1250 ml of 20% HCl in ethanol at such a rate that the temperature of the reaction flask is maintained at 20°–25° C. Following this neutralization, 250 ml of water is added and the mixture is stirred at the same temperature for 15 minutes. Then 1.8 L more of 20% HCl in ethanol is added to the reaction flask. The solution hazes after approximately 10–15 minutes. The stirring is continued for another 1.5 to 2 hours. The solid formed is collected by filtration and washed with cold ethanol portionwise. The overall yield of the pure compound is 90–96% starting from DAG (Example 1) with a purity of greater than 99.4%.

The claimed invention is:

1. A solvent-free method for synthesizing 1,2:5,6-di-O-isopropylidene-3-O-3'-(N',N'-dimethylamino-n-propyl)-α,D-glucofuranose comprising the steps of:
    forming, in the absence of solvent, a single mixture containing 1,2:5,6-di-O-isopropylidene-α,D-glucofuranose, a halodimethylaminopropane, and an anhydrous alkali base;
    heating said mixture to a temperature sufficient to allow said mixture to react;
    maintaining said mixture at a temperature of at least about 110° C. for a time sufficient to form 1,2:5,6-di-O-isopropylidene-3-O-3'-(N',N'-dimethylamino-n-propyl)-α,D-glucofuranose and drive off any water produced;
    removing any unreacted halodimethylaminopropane from said mixture; and
    recovering said 1,2:5,6-di-O-isopropylidene-3-O-3'-(N',N'-dimethylanmino-n-propyl)-α,D-glucofuranose.

2. The method of claim 1, wherein said mixture contains 0.1–0.2 molar excess of said halodimethylaminopropane and 2 molar excess of said anhydrous alkali base.

3. The method of claim 2, wherein said halodimethylaminopropane is chlorodimethylaminopropane and said anhydrous alkali base is sodium hydroxide.

4. The method of claim 1, wherein said halodimethylaminopropane is chlorodimethylaminopropane and said anhydrous alkali base is sodium hydroxide.

5. The method of claim 2, wherein said removal step is accomplished under reduced pressure.

6. The method of claim 2, wherein said recovery step comprises the steps of
    dissolving said 1,2:5,6-di-O-isopropylidene-3-O-3'-(N',N'-dimethylamino-n-propyl)-α,D-glucofuranose in an organic solvent which is immiscible with water;
    separating any solids from the resultant solution;

washing said solution with water to yield a liquid system containing a separate aqueous phase and a separate organic phase;

separating the aqueous phase from the organic phase; and recovering said 1,2:5,6-di-O-isopropylidene-3-O-3'-(N',N'-dimethylamino-n-propyl)-α,D-glucofuranose from the organic phase.

7. The method of claim 6, further comprising, after said recovery step, the step of selectively hydrolyzing said 1,2:5,6-di-O-isopropylidene-3-O-3'-(N',N'-dimethylamino-n-propyl)-α,D-glucofuranose to form 1,2-O-isopropylidene-3-O-3'-(N',N'-dimethylamino-n-propyl)-α,D-glucofuranose or the acid addition salt thereof.

8. The method of claim 3 wherein said selective hydrolysis is carried out using about 2 molar equivalents of $H_2O$ in 20% HCl in an ethanol environment.

9. The method of claim 8, further comprising the steps of washing said 1,2-O-isopropylidene-3-O-3'-(N',N'-dimethylamino-n-propyl)-α,D-glucofuranose or the acid addition salt thereof with alcohol; and drying said 1,2-O-isopropylidene-3-O-3'-(N',N'-dimethylamino-n-propyl)-α,D-glucofuranose or the acid addition salt thereof.

10. The method of claim 2, further comprising, after said recovery step, the step of selectively hydrolyzing said 1,2:5,6-di-O-isopropylidene-3-O-3'-(N',N'-dimethylamino-n-propyl)-α,D-glucofuranose to form 1,2-O-isopropylidene-3-O-3'-(N',N'-dimethylamino-n-propyl)-α,D-glucofuranose or the acid addition salt thereof.

11. The method of claim 1, further comprising, after said recovery step, the step of selectively hydrolyzing said 1,2:5,6-di-O-isopropylidene-3-O-3'-(N',N'-dimethylamino-n-propyl)-α,D-glucofuranose to form 1,2-O-isopropylidene-3-O-3'-(N',N'-dimethylamino-n-propyl)-α,D-glucofuranose or the acid addition salt thereof.

12. The method of claim 11, wherein said halodimethylaminopropane is chlorodimethylaminopropane, and said anhydrous alkali base is sodium hydroxide.

13. The method of claim 1, wherein said mixture is maintained at a temperature of from about 110° C. to about 135° C.

14. The process of claim 1, wherein said mixture is maintained at a temperature of from about 110° C. to about 120° C.

15. The process of claim 1, wherein said mixture is heated to a temperature of at least about 80° C.

16. The process of claim 1, wherein said time sufficient to form 1,2:5,6-di-O-isopropylidene-3-O-3'-(N',N'-dimethylamino-n-propyl)-α,D-glucofuranose and drive off any water produces is from about 30 minutes to about 120 minutes.

17. A solvent-free synthesis to prepare 1,2:5,6-di-O-isopropylidene-3-O-3'-(N',N'-dimethylamino-n-propyl)-α,D-glucofuranose by the following reaction:

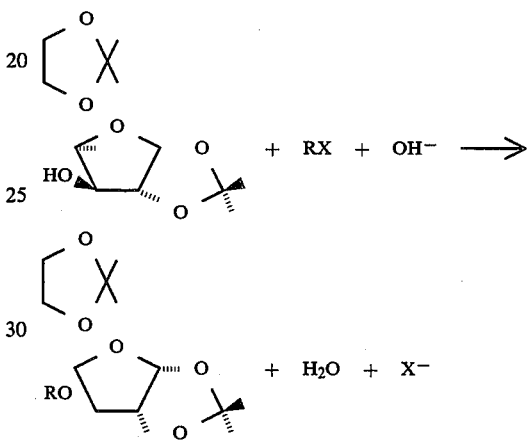

wherein R is a dimethylaminopropyl group, X is chloro, and the reactants are combined in a single mixture which is heated at a temperature of at least about 110° C. for a time sufficient to form 1,2:5,6-di-O-isopropylidene-3-O-3'-(N',N'-dimethylamino-n-propyl)-α,D-glucofuranose.

18. The method of claim 17, further comprising the step of selectively hydrolyzing said 1,2:5,6-di-O-isopropylidene-3-O-3'-(N',N'-dimethylamino-n-propyl)-α,D-glucofuranose to form 1,2-O-isopropylidene-3-O-3'-(N',N'-dimethylamino-n-propyl)-α,D-glucofuranose or the acid addition salt thereof.

* * * * *

UNITED STATES PATENT AND TRADEMARK OFFICE
CERTIFICATE OF CORRECTION

PATENT NO. : 5,344,924
DATED : September 6, 1994
INVENTOR(S) : Sudershan K. Arora It is certified that error appears in the above-indentified patent and that said Letters Patent is hereby corrected as shown below:

Column 5, line 50, before the reaction formula, insert --(I)--.

Column 6, line 5, before the reaction formula, insert --(II)--.

Column 9, lines 33-35, the formula should appear as follows:

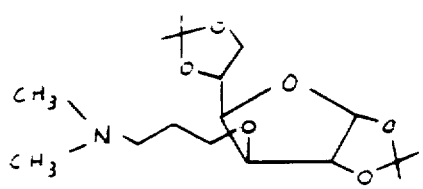

Claim 8, column 11, line 18, "claim 3" should read --claim 7--.

Claim 16, column 12, line 12, "produces" should read --produced--.

UNITED STATES PATENT AND TRADEMARK OFFICE
CERTIFICATE OF CORRECTION

PATENT NO. : 5,344,924
DATED : September 6, 1994
INVENTOR(S) : Sudershan K. Arora It is certified that error appears in the above-indentified patent and that said Letters Patent is hereby corrected as shown below:

Claim 17, column 12, lines 18-34, the formula should read appear as follows:

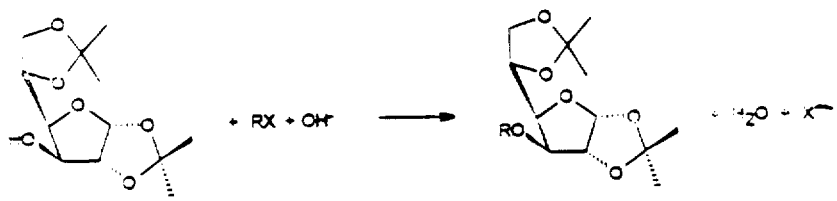

Signed and Sealed this

Thirtieth Day of May, 1995

Attest:

BRUCE LEHMAN

Attesting Officer      Commissioner of Patents and Trademarks